(12) United States Patent  
Rajkondawar et al.

(10) Patent No.: US 8,949,034 B2  
(45) Date of Patent: ***Feb. 3, 2015

(54) SYSTEM AND METHOD FOR HEALTH MONITORING USING REAL-TIME LOCATION

(75) Inventors: Parimal G. Rajkondawar, Madison, WI (US); Roger K. Erdman, Janesville, WI (US); David A. Johnson, McFarland, WI (US); William S. Nelson, Sun Prairie, WI (US); Paul D. Thompson, Madison, WI (US)

(73) Assignee: Technologies Holdings Corp., Houston, TX (US)

( * ) Notice: Subject to any disclaimer, the term of this patent is extended or adjusted under 35 U.S.C. 154(b) by 993 days.

This patent is subject to a terminal disclaimer.

(21) Appl. No.: 13/050,113

(22) Filed: Mar. 17, 2011

(65) Prior Publication Data

US 2012/0239303 A1    Sep. 20, 2012

(51) Int. Cl.
*A61D 17/00*    (2006.01)
*A01K 29/00*    (2006.01)

(52) U.S. Cl.
CPC .......... *A01K 29/005* (2013.01); *A61D 17/002* (2013.01)
USPC ...................................... 702/19; 119/51.02

(58) Field of Classification Search
CPC .................................................. A61D 17/002
USPC ........................................................... 702/19
See application file for complete search history.

(56) References Cited

U.S. PATENT DOCUMENTS

| | | | | |
|---|---|---|---|---|
| 4,618,861 | A * | 10/1986 | Gettens et al. | 340/10.41 |
| 8,132,538 | B1 * | 3/2012 | Schick et al. | 119/502 |
| 2002/0050248 | A1 * | 5/2002 | Pratt | 119/51.02 |
| 2002/0156394 | A1 * | 10/2002 | Mehrotra et al. | 600/551 |
| 2008/0314325 | A1 * | 12/2008 | Hempstead et al. | 119/51.02 |

FOREIGN PATENT DOCUMENTS

| | | | | |
|---|---|---|---|---|
| EP | 0 945 060 A2 | 9/1999 | ............. | A01K 11/00 |
| GB | 2 437 250 | 10/2007 | ............... | A61B 5/00 |
| WO | WO 2008/113556 A1 | 9/2008 | ............... | A61B 5/11 |
| WO | WO 2010/066429 A1 | 6/2010 | ............. | A01K 11/00 |

OTHER PUBLICATIONS

PCT Notification of Transmittal of the International Search Report and the Written Opinion of the International Searching Authority for International Application No. PCT/US2012/026235; 12 pages, May 18, 2012.

* cited by examiner

*Primary Examiner* — Bryan Bui
(74) *Attorney, Agent, or Firm* — Baker Botts L.L.P.

(57) ABSTRACT

In certain embodiments, a method includes storing location information associated with a dairy livestock. The stored location information includes a location of the dairy livestock within a free stall pen at each of a plurality of times during a time period. The method further includes determining, based on at least a portion of the stored location information, one or more movement parameters associated with the dairy livestock. The method further includes determining, based on the one or more movement parameters associated with the dairy livestock, whether the dairy livestock is likely unhealthy.

13 Claims, 3 Drawing Sheets

SYSTEM AND METHOD FOR HEALTH MONITORING USING REAL-TIME LOCATION

TECHNICAL FIELD

This invention relates generally to dairy farming and more particularly to a system and method for health monitoring using real-time location.

BACKGROUND OF THE INVENTION

For modern dairy milking operations to remain profitable, it may be important to maximize the efficiency of a herd of dairy livestock. In order to maximize efficiency of a herd of dairy livestock, it may be important to ensure that the herd of dairy livestock remains healthy and has a high reproductive efficiency. Accordingly, health monitoring and estrus detection for a herd of dairy livestock may be integral components of modern dairy milking operations. Current systems and methods supporting health monitoring and estrus detection, however, have proven inadequate in various respects.

SUMMARY OF THE INVENTION

According to embodiments of the present disclosure, disadvantages and problems associated with previous systems and methods for health monitoring may be reduced or eliminated.

In certain embodiments, a method includes storing location information associated with a dairy livestock. The stored location information includes a location of the dairy livestock within a free stall pen at each of a plurality of times during a time period. The method further includes determining, based on at least a portion of the stored location information, one or more movement parameters associated with the dairy livestock. The method further includes determining, based on the one or more movement parameters associated with the dairy livestock, whether the dairy livestock is likely unhealthy.

Particular embodiments of the present disclosure may provide one or more technical advantages. For example, certain embodiments of the present disclosure may facilitate an automated determination regarding whether each of the dairy livestock in a herd is likely unhealthy based on the movement of the dairy livestock within a free stall pen. Because a healthy herd of dairy livestock may have a greater quantity and/or quality of milk production, certain embodiments of the present disclosure may facilitate an increase in the overall milk output and/or quality for a herd of dairy livestock.

Certain embodiments of the present disclosure may include some, all, or none of the above advantages. One or more other technical advantages may be readily apparent to those skilled in the art from the figures, descriptions, and claims included herein.

BRIEF DESCRIPTION OF THE DRAWINGS

To provide a more complete understanding of the present invention and the features and advantages thereof, reference is made to the following description taken in conjunction with the accompanying drawings, in which.

DETAILED DESCRIPTION OF THE DRAWINGS

Figure 1:
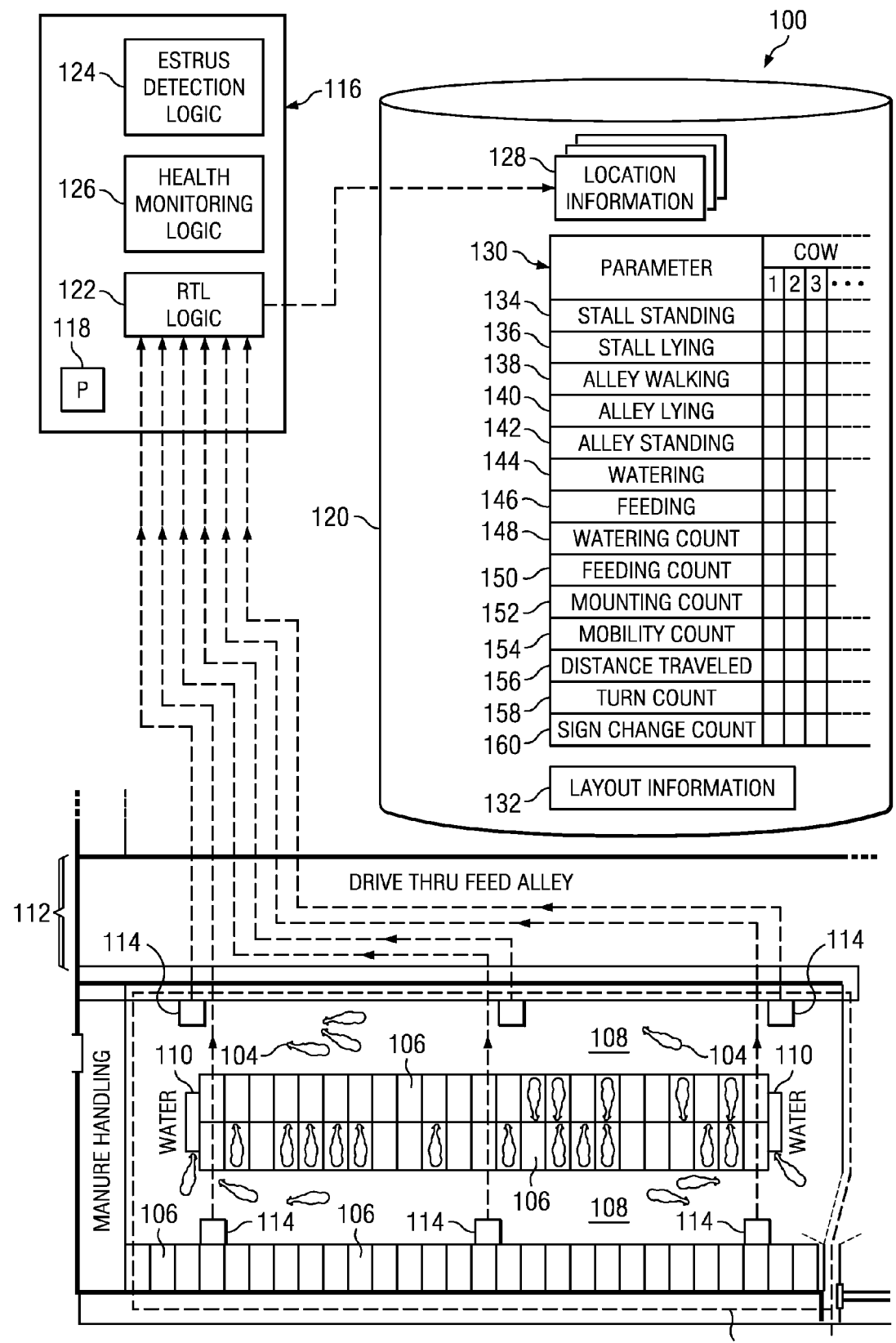
FIG. 1 illustrates a logical view of an example system for estrus detection and health monitoring using real-time location, according to certain embodiments of the present disclosure.

FIG. 1 illustrates a logical view of an example system 100 for estrus detection and health monitoring using real-time location, according to certain embodiments of the present disclosure. System 100 includes a free stall pen 102 housing a number of dairy livestock 104. Free stall pen 102 may be configured to include a number of stalls 106, walking lanes 108, and water troughs 110, and may be positioned adjacent to a feed lane 112. System 100 further includes a number of identification devices 114 positioned throughout free stall pen 102, each identification device 114 being configured to (1) read tags affixed to each of the dairy livestock 104, and (2) communicate with a controller 116. Although this particular implementation of system 100 is illustrated and primarily described, the present disclosure contemplates any suitable implementation of system 100 according to particular needs. Additionally, although the present disclosure contemplates free stall pen 102 housing any suitable dairy livestock 104 (e.g., cows, goats, sheep, water buffalo, etc.), the remainder of this description is detailed with respect to dairy cows.

Free stall pen 102 may include any suitable number of walls dividing free stall pen 102 into a number of stalls 106 and a number walking lanes 108. The walls of free stall pen 102 may be constructed of any suitable materials arranged in any suitable configuration operable to manage the movement of dairy cows 104. For example, the walls of free stall pen 102 may each include any number and combination of posts, rails, tubing, rods, connectors, cables, wires, and/or beams operable to form a substantially planar barricade such as a fence, wall, and/or other appropriate structure suitable to manage the movement of dairy cows 104. Free stall pen 102 may additionally include a number of water troughs 110 each positioned at any suitable location within free stall pen 102 such that dairy cows 104 may access drinking water.

Free stall pen 102 may be positioned adjacent to a feed lane 112. Feed lane 112 may be configured to permit a vehicle to pass through feed lane 112 and distribute feed for dairy cows 104 located in free stall pen 102. For example, feed lane 112 may be separated from free stall pen 102 by a wall comprising a number of slots sized such that dairy cows 104 may extend their heads into feed lane 112 and eat feed distributed in feed lane 112.

A number of identification devices 114 may be positioned at various locations within and/or adjacent to free stall pen 102. Although a particular number of identification devices 114 are illustrated as being positioned at particular locations within free stall pen 102, the present disclosure contemplates any suitable number of identification devices 114 located at any suitable positions within and/or adjacent to free stall pen 102, according to particular needs.

Identification devices 114 may each include any suitable device operable to receive a signal from a tag affixed to a dairy cow 104 (e.g., an ear tag) located in free stall pen 102. In response to a signal received from a tag affixed to a dairy cow 104, identification devices 114 may generate a signal corresponding to that tag for communication to controller 116 (described below). Communication between identification devices 114 and tags affixed to dairy cows 104 may be facilitated by any suitable technology, including, for example, passive radio-frequency identification (RFID), active RFID, Wi-Fi, Bluetooth, ultra-wide band (UWB), ZigBee, acoustic locating, and computer vision. In certain embodiments, a generated signal corresponding to a tag affixed to a dairy cow 104 may include (1) an identification number related to the dairy cow 104, (2) the distance, angle, and/or other information concerning the location of the dairy cow 104 relative to the identification device 114 generating the signal, (3) an identification of the identification device 114 generating the signal, and/or (4) a timestamp.

Identification devices 114 may be communicatively coupled (e.g., via a network facilitating wireless or wireline communication) to controller 116. Controller 116 may include one or more computer systems at one or more locations. Each computer system may include any appropriate input devices (such as a keypad, touch screen, mouse, or other device that can accept information), output devices, mass storage media, or other suitable components for receiving, processing, storing, and communicating data. Both the input devices and output devices may include fixed or removable storage media such as a magnetic computer disk, CD-ROM, or other suitable media to both receive input from and provide output to a user. Each computer system may include a personal computer, workstation, network computer, kiosk, wireless data port, personal data assistant (PDA), one or more processors within these or other devices, or any other suitable processing device. In short, controller 116 may include any suitable combination of software, firmware, and hardware.

Controller 116 may additionally include one or more processing modules 118 and one or more memory modules 120 (each referred to in the singular throughout the remainder of this description). Processing module 118 may include one or more microprocessors, controllers, or any other suitable computing devices or resources and may work, either alone or with other components of system 100, to provide a portion or all of the functionality of system 100 described herein. Memory module 120 may take the form of volatile or non-volatile memory including, without limitation, magnetic media, optical media, random access memory (RAM), read-only memory (ROM), removable media, or any other suitable memory component.

Controller 116 may additionally include real-time location (RTL) logic 122, estrus detection logic 124, and health monitoring logic 126 (e.g., each stored memory module 120). RTL logic 122 (which, in combination with identification devices 114 and the plurality of tags affixed to the plurality of dairy cows 104, may be referred to as a real-time location system (RTLS)) may include any information, logic, and/or instructions stored and/or executed by controller 116 to determine location information 128 associated with dairy cows 104 in free stall pen 102 based on signals received from identification devices 114 (as described in further detail below). Estrus detection logic 124 may include any information, logic, and/or instructions stored and/or executed by controller 116 to determine, based on the location information 128 associated with a particular dairy cow 104 generated by RTL logic 122, whether the particular dairy cow 104 is likely to be in estrus (as described in further detail below). Health monitoring logic 126 may include any information, logic, and/or instructions stored and/or executed by controller 116 to determine, based on the location information 128 associated with a particular dairy cow 104 generated by RTL logic 122, whether the particular dairy cow 104 is likely unhealthy (as described in further detail below). Although certain functionality is described below as being associated with RTL logic 122, estrus detection logic 124, or health monitoring logic 126, the present disclosure contemplates the functionality described below as being combined or divided among any suitable logic, according to particular needs.

Controller 116 may be operable to receive signals generated by identification devices 114. In certain embodiments, controller 116 may receive signals corresponding to each dairy cow 104 in free stall pen 102 from each identification device 114. Furthermore, for a particular dairy cow 104, controller 116 may receive signals from each identification device 114 at or about the same time and at regular intervals (e.g., every fifteen seconds). For example, for a particular dairy cow 104 at a particular time, controller 116 may receive signals generated by a number of identification devices 114 (e.g., each signal identifying the particular dairy cow 104 and the distance the particular dairy cow 104 is located from the corresponding identification device 114). Based on the received signals, controller 116 may determine location information 128 associated with the particular dairy cow 104 at the particular time (e.g., using RTL logic 122, as described below).

In certain embodiments, RTL logic 122 may be operable to process signals received from identification devices 114 in order to determine location information 128 associated with dairy cows 104 in free stall pen 102. As described above, a particular subset of the received signals may be generated by the identification devices 114 at approximately the same time and may identify the same particular dairy cow 104. Each of the signals of the particular subset may additionally include information about the position of the particular dairy cow 104 relative to the corresponding identification device 114 (e.g., distance, angle, etc.). Based on one or more of the subset of received signals, RTL logic 122 may determine a coordinate location of the particular dairy cow 104 within free stall pen 102. In certain embodiments, the determined coordinate location may be an (X,Y) location within the free stall pen 102. In certain other embodiments, the determined coordinate location may be an (X,Y,Z) location within the free stall pen 102.

As just one example, RTL logic 122 may determine a coordinate location of the particular dairy cow 104 within free stall pen 102 using triangulation (based on at least three of the subset of received signals). Because each of the at least three signals may include information about the position of the particular dairy cow 104 (e.g., distance and/or angle) relative to the corresponding identification device 114 and the location of each corresponding identification device 114 within free stall pen 102 may be known, the coordinate location (e.g., an (X,Y) location, an (X,Y,Z) location, or any other suitable coordinate location) of the particular dairy cow 104 within free stall pen 102 may be determined.

Furthermore, because controller 116 may receive signals from identification devices 114 for each dairy cow 104 on a periodic basis (e.g., every fifteen seconds), location information 128 may be generated for each dairy cow 104 in free stall pen 102 at each of a number of times during a particular time period (e.g., every fifteen seconds over a one hour period). The generated location information 128 associated with each dairy cow 104 may then be stored (e.g., in memory module 120 or any other suitable location in system 100) such that the location information 128 may be later accessed (e.g., by estrus detection logic 124 and health monitoring logic 126, as described in further detail below).

In certain embodiments, estrus detection logic 124 may be operable to access location information 128 associated with each dairy cow 104 in free stall pen 102 and determine, based on at least a portion of that location information 128, one or more movement parameters 130 associated with each dairy cow 104. The determined movement parameters 130 for dairy cows 104 may be stored (e.g., in memory module 120) such that changes in the movement parameters 130 may be assessed over time. Because the movement of a dairy cow 104 within free stall pen 102 (as reflected by the movement parameters 130, which are described in detail below) may be indicative of whether the dairy cow 104 is in estrus, the movement parameters 130 may be used by estrus detection logic 124 to determine whether the dairy cow 104 is likely to be in estrus (as described below).

In certain embodiments, the movement parameters 130 for a particular dairy cow 104 may include a percentage of a particular time period (e.g., one hour) the particular dairy cow 104 spent in each of a number of areas of free stall pen 102. For example, the movement parameters 130 may include (1) a percentage of time the particular dairy cow 104 spent standing in a stall 106 of free stall pen 102 (stall standing parameter 134), (2) a percentage of time the particular dairy cow 104 spent lying in a stall 106 of free stall pen 102 (stall lying parameter 136), (3) a percentage of time the particular dairy cow 104 spent walking in a walking alley 108 of free stall pen 102 (alley walking parameter 138), (4) a percentage of time the particular dairy cow 104 spent lying in a walking alley 108 of free stall pen 102 (alley lying parameter 140), (5) a percentage of time the particular dairy cow 104 spent standing in a walking alley 108 of free stall pen 102 (alley standing parameter 142) (6) a percentage of time the particular dairy cow 104 spent near a water trough 110 (watering parameter 144), and/or (7) a percentage of time the particular dairy cow 104 spent near feed lane 112 (feeding parameter 146).

The above-described movement parameters 130 for a particular dairy cow 104 may be determined by comparing the location information 128 for the particular dairy cow 104 collected during a particular time period (including a number of coordinate locations for the particular dairy cow 104 at a number of discrete times during the particular time period, as described above) with layout information 132 for free stall pen 102 (e.g., stored in memory module 120). In certain embodiments, layout information 132 for free stall pen 102 may include coordinate locations defining the corners of each stall 106 (and thus defining the area within each stall 106), coordinate locations defining the corners of each walking lane 108 (and thus defining the area within each walking lane 108), coordinate locations defining the corners of the area around each water trough 110 (and thus defining a watering area), and the corners of the area near feed lane 112 (and thus defining a feeding area). For each coordinate location for the particular dairy cow 104 within these defined areas, the area in which the particular dairy cow 104 is located at each discrete time during the time period may be determined.

For example, location information 128 for a particular dairy cow 104 may include coordinate locations of the particular dairy cow 104 at discrete times (e.g., every fifteen seconds) during a particular time period (e.g., one hour). By comparing each (X,Y) coordinate location of the particular dairy cow 104 with layout information 132 for free stall pen 102, the position of the particular dairy cow 104 within free stall pen 102 may be determined at each discrete time during the time period. Moreover, if it is assumed that the position of the particular dairy cow 104 remains constant from one discrete time to the next (e.g., for the fifteen second time period until a new coordinate location for the particular dairy cow 104 is available), a percentage of the particular time period that the particular dairy cow 104 spent in various locations within the free stall pen 102 may be determined. Furthermore, in embodiments in which the coordinate location for the particular dairy cow 104 includes a (Z) location, a percentage of the particular time period that the particular dairy cow 104 spent standing versus lying at each location may additionally be determined (as a (Z) location for the particular dairy cow 104 in both a standing and lying position may be known). From this information, the above-described movement parameters 130 (e.g., a stall standing parameter 134, a stall lying parameter 136, an alley walking parameter 138, an alley lying parameter 140, an alley standing parameter 142, a watering parameter 144, and a feeding parameter 146) may be determined.

In certain embodiments, the movement parameters 130 for a particular dairy cow 104 may additionally include a watering count 148 and a feeding count 150. The watering count 148 may correspond to the number of times during a time period that the particular dairy cow 104 moves within a predetermined distance (e.g., five feet) of a water trough 110. Similarly, the feeding count 150 may correspond to the number of times during a time period that the particular dairy cow 104 moves within a predetermined distance (e.g., five feet) of feed lane 112. Additionally, in embodiments in which location information 128 includes a (Z) coordinate location, movement parameters 130 for a particular dairy cow 104 may additionally include a mounting count 152. The mounting count 152 may correspond to the number of times during a particular time period that the (Z) coordinate location of the particular dairy cow 104 increasing above a particular threshold (indicating that the particular dairy cow 104 has mounted another dairy cow 104).

In certain embodiments, the movement parameters 130 for a particular dairy cow 104 may additionally include a mobility count 154. The mobility count 154 may correspond to the number of times during a time period that the particular dairy cow 104 moves more than a predetermined distance (e.g., five feet) between consecutive discrete times for which a coordinate location is available for the particular dairy cow 104 (e.g., during the fifteen second interval between times that identification devices 114 generate signals corresponding to the particular dairy cow 104). As just one example, in embodiments in which the location information 128 for the particular dairy cow 104 includes (X,Y) location for the particular dairy cow 104 at a number of discrete times (t), the mobility count 154 may be determined as follows:

If $[X(t+1)-X(t)]>5$ feet or $[Y(t+1)-Y(t)]>5$ feet then increase mobility count by 1

In certain embodiments, the mobility count 154 may be normalized to determine a mobility count per hour by dividing the determined mobility count 154 by the number of hours in the time period during which the mobility count 154 was determined.

In certain embodiments, the movement parameters 130 for a particular dairy cow 104 may additionally include a distance traveled 156 by the particular dairy cow 104 during a time period. As just one example, in embodiments in which the location information 128 for the particular dairy cow 104 includes (X,Y) location for the particular dairy cow 104 at a number of discrete times (t), the distance traveled 156 by the particular dairy cow 104 may be determined as follows:

$$Dist.Trav. = \sum_{t=1}^{n} \sqrt{(X(t+1)-X(t))^2 + (Y(t+1)-Y(t))^2}$$

In certain embodiments, the distance traveled 156 by the particular dairy cow 104 in a time period may be normalized to determine a distance traveled per hour by dividing the determined distance traveled 156 by the number of hours in the time period for which the distance traveled 156 was determined.

In certain embodiments, the movement parameters 130 for a particular dairy cow 104 may additionally include a turn count 158. The turn count 158 may correspond to the number of times during a time period that the particular dairy cow 104 changes direction between consecutive discrete times for which a coordinate location is available for the particular dairy cow 104 (e.g., the difference in angular direction of the particular dairy cow 104 from discrete time to the next changes less than 90° or more than 270°). As just one example, in embodiments in which the location information for the particular dairy cow 104 includes (X,Y) location for the particular dairy cow 104 at a number of discrete times (t), the turn count 158 for the particular dairy cow 104 may be determined as follows:

If angle<90° or angle>270° then increase turn count by 1
where:

$$\text{angle} = \arccos\left[\frac{c^2 - b^2 - a^2}{2ba}\right]$$

$$a = \sqrt{(Y(t+1)-Y(t))^2 + (X(t+1)-X(t))^2}$$

$$b = \sqrt{(Y(t+2)-Y(t+1))^2 + (X(t+2)-X(t+1))^2}$$

$$c = \sqrt{(Y(t+2)-Y(t))^2 + (X(t+2)-X(t))^2}$$

In certain embodiments, the turn count 158 may be normalized to determine a number of turns per hour by dividing the determined turn count 158 by the number of hours in the time period for which the turn count 158 was determined.

In certain embodiments, the movement parameters 130 for a particular dairy cow 104 may additionally include a sign change count 160. Like the turn count 158, the sign change count 160 may correspond to the number of times during a time period that the particular dairy cow 104 changes direction between consecutive discrete times for which a coordinate location is available for the particular dairy cow 104. As just one example, in embodiments in which the location information for the particular dairy cow 104 includes (X,Y) location for the particular dairy cow 104 at a number of discrete times (t), the sign change count 160 for the particular dairy cow 104 may be determined as follows:

If

[X(t+1)−X(t)]>0 and [X(t+2)−X(t+1)]<0 (or vice versa)

or

[Y(t+1)−Y(t)]>0 and [Y(t+2)−Y(t+1)]<0 (or vice versa)

then increase sign change count by 1

In certain embodiments, the sign change count 160 may be normalized to determine a number of sign changes per hour by dividing the determined sign change count 160 by the number of hours in the time period for which the sign change count 160 was determined.

Estrus detection logic 124 may additionally be operable to determine, based on one or more of the above-described movement parameters 130 associated with dairy cows 104 (determined based on coordinate locations for the particular dairy cow 104 during a particular time period, as described above), which of the dairy cows 104 are likely to be in estrus at a given time.

For example, estrus detection logic 124 may determine if a particular dairy cow 104 is likely to be in estrus by comparing a "heat index" for the particular dairy cow 104 (described below) with a baseline heat index. In certain embodiments, the heat index for a particular dairy cow 104 may correspond to the product of an alley walking parameter 138 and a normalized mobility count 154 (e.g., heat index=(alley walking parameter)×(mobility count/hour)). In such embodiments, the heat index may be indicative of the amount of movement of the particular dairy cow 104, with a certain amount of increase in movement of the particular dairy cow 104 (e.g., 250% over a baseline, as described below) being an indicator that the particular dairy cow 104 is in estrus.

In certain other embodiments, the heat index for a particular dairy cow 104 may correspond to a function of stall standing parameter 134, stall lying parameter 136, alley walking parameter 138, alley lying parameter 140, ally standing parameter 142, watering parameter 144, feeding parameter 146, watering count 148, feeding count 150, mounting count 152, mobility count 154, distance traveled 156, turn count 158, and/or sign change count 160. As just one example, the heat index may be calculated as follows:

Heat Index=$a$*(stall standing parameter 134)+$b$*(stall lying parameter 136)+$c$*(alley walking parameter 138)+$d$*(alley lying parameter 140)+$e$*(ally standing parameter 142)+$f$*(watering parameter 144)+$g$*(feeding parameter 146)+$h$*(watering count 148)+$i$*(feeding count 150)+$j$*(mounting count 152)+$k$*(mobility count 154)+$l$*(distance traveled 156)+$m$*(turn count 158)+$n$*(sign change count 160)

where:
a=−10
b=−10
c=35
d=−10
e=−10
f=0
g=−20
h=10
i=−10
j=20
k=30
l=40
m=20
n=15

In such embodiments, the heat index may be indicative of an increase in certain activity of the particular dairy cow 104 (e.g., walking in walking lanes 108, pacing, and/or mounting other dairy cows 104), with an increase in such activity being an indicator that the particular dairy cow 104 is in estrus. Although particular constants a-n are listed as being used to calculate the heat index for example purposes, the present disclosure contemplates any suitable constants, according to particular needs.

If the heat index for particular dairy cow 104 is greater than the baseline heat index by more than a predefined amount (e.g., 250%), estrus detection logic 124 may determine that the particular dairy cow 104 is likely to be in estrus (as such an increase may indicate either that (1) the amount of movement of the particular dairy cow 104 has increased or (2) the particular dairy cow 104 is spending time in those portions of the free stall pen 102 in which a dairy cow 104 likely to be in estrus is likely to be located, such as walking lanes 108). The baseline heat index may be (1) a heat index for the particular dairy cow 104 during a previous time period (e.g., the previous twenty-four hours), (2) an average heat index for one or more other dairy cows 104 in free stall pen 102 during a previous time period (e.g., the previous twenty-four hours), (3) a user defined baseline heat index, or (4) any other suitable baseline heat index, according to particular needs. In certain embodiments, the baseline heat index may take into account the ambient conditions in the free stall pen 102 (e.g., temperature), as the movement of dairy cows 104 within free stall pen 102 may vary based on those conditions.

As another example, estrus detection logic 124 may compare a distance traveled 156 by the particular dairy cow 104 (e.g., a distance traveled per hour during a particular time period, as described above) with a baseline distance traveled. If the distance traveled 156 by the particular dairy cow 104 is greater than the baseline distance traveled by more than a predefined amount (e.g., 250%), estrus detection logic 124 may determine that the particular dairy cow 104 is likely to be in estrus (as an increase in movement of the particular dairy cow 104 may be an indicator that the particular dairy cow 104 is in estrus). The baseline distance traveled may be (1) a distance traveled by the particular dairy cow 104 during a previous time period (e.g., the distance traveled per hour during the previous twenty-four hours), (2) an average distance traveled by one or more other dairy cows 104 in free stall pen 102 during a previous time period (e.g., the average distance traveled per hour during the previous twenty-four hours), (3) a user defined baseline distance traveled, or (4) any other suitable baseline distance traveled, according to particular needs. In certain embodiments, the baseline distance traveled may take into account the ambient conditions in the free stall pen 102 (e.g., temperature), as the movement of dairy cows 104 within free stall pen 102 may vary based on those conditions.

As yet another example, estrus detection logic 124 may compare a "turn index" for a particular dairy cow 104 (described below) with a baseline turn index. In certain embodiments, the turn index may correspond to the sum of turn count 158 and sign change count 160 (e.g., turn index=(turn count)+(sign change count)). In such embodiments, the turn index may be indicative of pacing by the particular dairy cow 104, which may be an indicator that the particular dairy cow 104 is in estrus.

If the turn index for particular dairy cow 104 is greater than the baseline turn index by more than a predefined amount (e.g., 250%), estrus detection logic 124 may determine that the particular dairy cow 104 is likely to be in estrus (as such an increase may be indicative of an increase in pacing by the particular dairy cow 104, which may be indicative of estrus). The baseline turn index may be (1) a turn index for the particular dairy cow 104 during a previous time period (e.g., the previous twenty-four hours), (2) an average turn index for one or more other dairy cows 104 in free stall pen 102 during a previous time period (e.g., the previous twenty-four hours), (3) a user defined baseline turn index, or (4) any other suitable baseline turn index, according to particular needs. In certain embodiments, the baseline turn index may take into account the ambient conditions in the free stall pen 102 (e.g., temperature), as the movement of dairy cows 104 within free stall pen 102 may vary based on those conditions.

Having determined that a particular dairy cow 104 is likely to be in estrus, estrus detection logic 124 may be further operable to confirm that determination. For example, in response to a determination that a particular dairy cow 104 is likely to be in estrus, estrus detection logic 124 may access stored information associated with the particular dairy cow 104 (e.g., stored in memory module 120) to determine if the particular dairy cow 104 is near the twenty-first day of her cycle. A determination that the particular dairy cow 104 is near the twenty-first day of her cycle may provide further confirmation that the particular dairy cow 104 is likely to be in estrus.

As an additional example, in response to a determination that a particular dairy cow 104 is likely to be in estrus, estrus detection logic 124 may initiate the generation of a signal to be communicated to identification devices 114, the signal causing identification devices 114 to increase the frequency with which the tag of the particular dairy cow 104 is read (e.g., from fifteen seconds to five seconds). As a result, updated location information 128 may be generated by RTL logic 122 (including coordinate locations for the particular dairy cow 104 at more closely spaced intervals). Based on that updated location information 128, one or more of the above-described movement parameters 130 may be recalculated, and estrus detection logic 124 may make a subsequent determination regarding whether the particular dairy cow 104 is likely to be in estrus (in a manner substantially similar to that described above) in order to further confirm the original estrus determination. In certain embodiments, the frequency with which the tag of the particular dairy cow 104 is read may revert to the default frequency (e.g., fifteen seconds) in response to the expiration of a predetermined period of time (e.g., one hour), in response to user input, or in response to any other suitable trigger.

As yet another example, in response to a determination that a particular dairy cow 104 is likely to be in estrus, estrus detection logic 124 may access location information 128 for other dairy cows 104 in free stall pen 102 to identify those other dairy cows 104 within a predefined distance of the particular dairy cow 104. Estrus detection logic 124 may monitor location information 128 of the identified other dairy cows 104 to determine if there are any increases in the (Z) coordinate location for the identified other dairy cows 104. An increase in the (Z) coordinate location of another dairy cow 104 located near the particular dairy cow 104 may indicate that the other dairy cow 104 is mounting the particular dairy cow 104, which may provide further confirmation that the particular dairy cow 104 is in estrus.

As yet another example, in response to a determination that a particular dairy cow 104 is in estrus, estrus detection logic 124 may access location information 128 for other dairy cows 104 in free stall pen 102 to identify those other dairy cows 104 within a predefined distance of the particular dairy cow 104. Estrus detection logic 124 may then monitor the location of the identified other dairy cows 104 to determine if any remain within a predefined distance of the particular dairy cow 104 for an extended period of time (e.g., one hour). Certain of the identified other dairy cows 104 remaining near the particular dairy cow 104 may indicate the presence of a sexually active group (SAG) (i.e., a group of dairy cows 104 which are each in estrus). Determining that the particular dairy cow 104 is a member of a SAG may provide further confirmation that the particular dairy cow 104 is likely to be in estrus.

Having determined that one or more dairy cows 104 are likely to be in estrus (and possibly subsequent to confirming those determinations), estrus detection logic 124 may create exception reports to be stored in association with the one or more dairy cows 104 (e.g., in memory module 120). Additionally or alternatively, estrus detection logic 124 may initiate the communication of reports (e.g., emails) to the farmer for each of the one or more dairy cows 104 such that the farmer may further monitor the one or more dairy cows 104 and/or remove the one or more dairy cows 104 from the free stall pen 102 for breeding. In certain embodiments, a report communicated to a farmer may indicate the relative strength of the estrus determination.

In certain embodiments, health monitoring logic 126 may be operable to access location information 128 associated with each dairy cow 104 in free stall pen 102 and determine, based on at least a portion of that location information, one or more movement parameters 130 associated with each dairy cow 104. For example, health monitoring logic 126 may determine movement parameters 130 including a percentage of a particular time period (e.g., one hour) the dairy cows 104 spent in each of a number of areas of free stall pen 102. For example, health monitoring logic 126 may determine a stall standing parameter 134, a stall lying parameter 136, an alley walking parameter 138, an alley lying parameter 140, an alley standing parameter 142, a watering parameter 144, a feeding parameter 146, a watering count 148, and/or a feeding count 150 in a manner substantially similar to that described above. The determined movement parameters 130 for dairy cows 104 may be stored (e.g., in memory module 120) such that changes in the movement parameters 130 may be assessed over time. Because the movement of a dairy cow 104 within free stall pen 102 may be indicative of whether the dairy cow 104 is likely unhealthy, the movement parameters may be used by health monitoring logic 126 to determine if one or more dairy cows 104 are unhealthy (as described below).

Although health monitoring logic 126 and estrus detection logic 124 are each described as determining common movement parameters for dairy cows 104, the present disclosure contemplates those parameters being calculated by health monitoring logic 126, estrus detection logic 124, or by any other suitable logic (e.g., RTL logic 122) such that the movement parameters may be shared between health monitoring logic 126 and estrus detection logic 124.

Health monitoring logic 126 may additionally be operable to determine, based on one or more of the above-described movement parameters 130 associated with dairy cows 104 (determined based coordinate locations for the particular dairy cow 104 during a particular time period, as described above), which of the dairy cows 104 are unhealthy at a given time. For example, health monitoring logic 126 may compare a "health index" for a particular dairy cow 104 (described below) with a baseline health index. In certain embodiments, the health index for the particular dairy cow 104 may correspond to a function of a stall standing parameter 134, a stall lying parameter 136, an alley walking parameter 138, an alley lying parameter 140, an alley standing parameter 142 a watering parameter 144, a feeding parameter 146, a watering count 148, and/or a feeding count 150. As just one example, the health index may be calculated as follows:

Health Index=$a^*$(stall standing parameter 134)+$b^*$(stall lying parameter 136)+$c^*$(alley walking parameter 138)+$d^*$(alley lying parameter 140)+$e^*$(ally standing parameter 142)+$r^*$(watering parameter 144)+$g^*$(feeding parameter 146)+$h^*$(watering count 148)+$i^*$(feeding count 150)+$j^*$(mounting count 152)+$k^*$(mobility count 154)+$l^*$(distance traveled 156)+$m^*$(turn count 158)+$n^*$(sign change count 160)

where:
a=0
b=0
c=−20
d=20
e=0
f=0
g=−40
h=0
i=0
j=0
k=0
l=−30
m=0
n=0

In such embodiments, the health index may be indicative of an amount of time the particular dairy cow 104 spent in each of the various portions of free stall pen 102, with an increase in activity in certain portions of free stall pen 102 (e.g., an increase in the amount of time spent lying in walking alleys 108) being an indicator that the particular dairy cow 104 is unhealthy. Although particular constants a-n are listed as being used to calculate the health index for example purposes, the present disclosure contemplates any suitable constants, according to particular needs.

If the health index for particular dairy cow 104 is greater than the baseline health index by more than a predefined amount (e.g., 250%), health monitoring logic 126 may determine that the particular dairy cow 104 is likely unhealthy. The baseline health index may be (1) a health index for the particular dairy cow 104 during a previous time period (e.g., the previous twenty-four hours), (2) an average health index for one or more other dairy cows 104 in free stall pen 102 during a previous time period (e.g., the previous twenty-four hours), (3) a user defined baseline health index, or (4) any other suitable baseline health index, according to particular needs.

Having determined that a particular dairy cow 104 is likely unhealthy, health monitoring logic 126 may be operable to confirm that determination. For example, health monitoring logic 126 may initiate the generation of a signal to be communicated to identification devices 114, the signal causing identification devices 114 to increase the frequency with which the tag of the particular dairy cow 104 is read (e.g., from fifteen seconds to five seconds). As a result, updated location information 128 may be generated by RTL logic 122 (including coordinate locations for the particular dairy cow 104 at more closely spaced intervals). Based on that updated location information 128, one or more of the above-described movement parameters 130 may be recalculated, and health monitoring logic 126 may make a subsequent determination regarding whether the particular dairy cow 104 is likely unhealthy (in a manner substantially similar to that described above) in order to further confirm the original unhealthy determination. In certain embodiments, the frequency with which the tag of the particular dairy cow 104 is read may revert to the default frequency (e.g., fifteen seconds) in response to the expiration of a predetermined period of time (e.g., one hour), in response to user input, or in response to any other suitable trigger.

Having determined that one or more dairy cows 104 are unhealthy (and possibly subsequent to confirming those determinations), health monitoring logic 126 may create exception reports to be stored in association with the one or more dairy cows 104 (e.g., in memory module 120). Additionally or alternatively, health monitoring logic 126 may initiate the communication of reports (e.g., emails) to the farmer for each of the one or more dairy cows 104 such that the farmer may further monitor the one or more dairy cows 104 and/or remove the one or more dairy cows 104 from the free stall pen 102 for medical attention. In certain embodiments, a report communicated to a farmer may indicate the relative strength of the determination that a dairy cow 104 is likely unhealthy.

Although a particular implementation of system 100 is illustrated and primarily described, the present disclosure contemplates any suitable implementation of system 100, according to particular needs.

Figure 2:
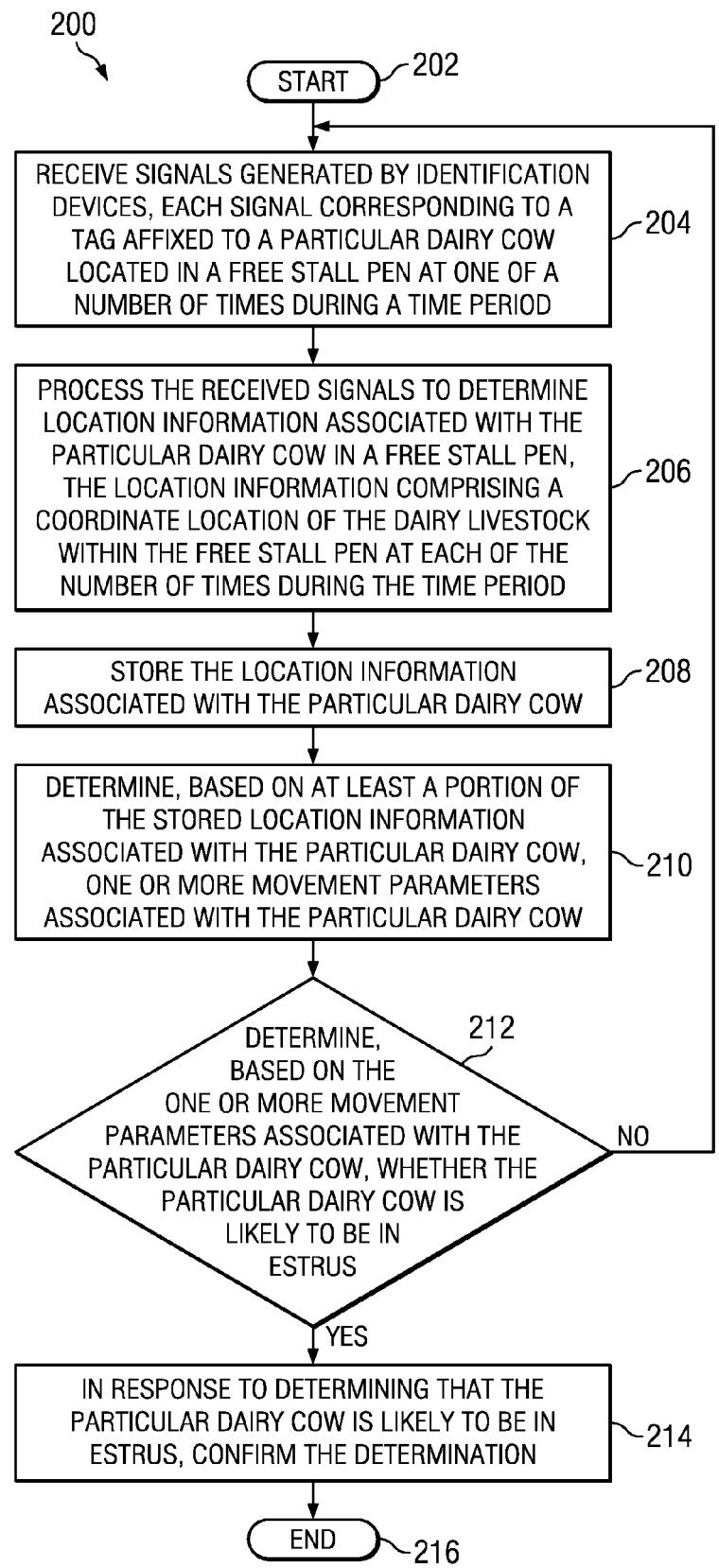
FIG. 2 illustrates an example method for estrus detection using real-time location, according to certain embodiments of the present disclosure.

FIG. 2 illustrates an example method 200 for estrus detection, according to certain embodiments of the present disclosure. Although method 200 is described with regard to a particular dairy cow 104, the present disclosure contemplates a substantially similar method being performed with regard to each of the plurality of dairy cows 104 in free stall pen 102.

The method begins at step 202. At step 204, controller 116 receives signals generated by a number of the identification devices 114 positioned at various locations in and/or around free stall pen 102. Each signal corresponds to a tag affixed to a particular dairy cow 104 located in a free stall pen 102 at one of a number of times during a time period. At step 206, controller 116 processes the received signals (e.g., using RTL logic 122, described above) to determine location information 128 associated with the particular dairy cow 104. The determined location information 128 may include a coordinate location of the dairy livestock within the free stall pen 102 at each of the number of times during the time period (e.g., every fifteen seconds during a one hour time period). For example, each of the received signals may include information about the distance from a corresponding identification device 114 to the particular dairy cow 104. By processing together those signals generated at or near the same time (e.g., using triangulation based on the distance information and a known location for each of the corresponding identification devices 114), controller 116 may determine a coordinate location (e.g., an (X,Y) location, an (X,Y,Z) location, or any other suitable coordinate location) of the particular dairy cow 104 within free stall pen 102 at each of the number of times during the time period.

At step 208, controller 116 may store the determined location information 128 associated with the particular dairy cow 104 (e.g., in memory module 120). At step 210, controller 116 may determine one or more movement parameters 130 associated with the particular dairy cow 104 (e.g., using estrus detection logic 124, described above) based on at least a portion of the stored location information 128 associated with the particular dairy cow 104. For example, the determined movement parameters 130 may include a stall standing parameter 134, a stall lying parameter 136, an alley walking parameter 138, and alley lying parameter 140, an alley standing parameter 142, a watering parameter 144, a feeding parameter 146, a watering count 148, a feeding count 150, a mounting count 152, a mobility count 154, a distance traveled 156, a turn count 158, and/or a sign change count 160 (each of which are described above with respect to FIG. 1)

At step 212, controller 116 may determine whether the particular dairy cow 104 is likely to be in estrus (e.g., using estrus detection logic 124, described above) based on the one or more movement parameters 130 associated with the particular dairy cow 104. For example, controller 116 may determine whether the particular dairy cow 104 is likely to be in estrus by comparing a heat index for the particular dairy cow 104 with a baseline heat index. If the heat index for particular dairy cow 104 is greater than the baseline heat index by more than a predefined amount (e.g., 250%), controller 116 may determine that the particular dairy cow 104 is likely to be in estrus.

In embodiments in which the heat index corresponds to the product of an alley walking parameter 138 and a normalized mobility count 154 (e.g., heat index=(alley walking parameter)×(mobility count/hour)), an increase in heat index may be indicative of an increase in movement of the particular dairy cow 104 (which may be an indicator that the particular dairy cow 104 is in estrus). In embodiments in which the heat index corresponds to a function of stall standing parameter 134, stall lying parameter 136, alley walking parameter 138, alley lying parameter 140, ally standing parameter 142, watering parameter 144, feeding parameter 146, watering count 148, feeding count 150, mounting count 152, mobility count 154, distance traveled 156, turn count 158, and/or sign change count 160, an increase in certain activity of the particular dairy cow 104 (e.g., walking in walking lanes 108, pacing, and/or mounting other dairy cows 104) may be an indicator that the particular dairy cow 104 is in estrus.

As another example, controller 116 may determine whether the particular dairy cow 104 is likely to be in estrus by comparing a distance traveled 156 by the particular dairy cow 104 (e.g., a distance traveled during a particular time period, as described above) with a baseline distance traveled. If the distance traveled 156 by the particular dairy cow 104 is greater than the baseline distance traveled by more than a predefined amount (e.g., 250%), estrus detection logic 124 may determine that the particular dairy cow 104 is likely to be in estrus (as an increase in movement of the particular dairy cow 104 may be an indicator that the particular dairy cow 104 is in estrus).

As yet another example, controller 116 may determine whether the particular dairy cow 104 is likely to be in estrus by comparing a turn index (e.g., turn index=(turn count/hour)×(sign change count/hour)) for a particular dairy cow 104 with a baseline turn index. If the turn index for particular dairy cow 104 is greater than the baseline turn index by more than a predefined amount (e.g., 250%), controller 116 may determine that the particular dairy cow 104 is likely to be in estrus (as such an increase may be indicative of an increase in pacing by the particular dairy cow 104, which may be indicative of estrus).

If controller 116 determines at step 212 that the particular dairy cow 104 is likely to be in estrus, the method proceeds to step 214. Otherwise, the method returns to step 204. At step 214, controller 116 may confirm the determination that the particular dairy cow 104 is likely to be in estrus. For example, controller 116 may confirm the estrus determination by accessing stored information associated with the particular dairy cow 104 (e.g., stored in memory module 120) to determine if the particular dairy cow 104 is near the twenty-first day of her cycle. As an additional example, controller 116 may initiate the generation of a signal to be communicated to identification devices 114, the signal causing identification devices 114 to increase the frequency with which the tag of the particular dairy cow 104 is read (e.g., from fifteen seconds to five seconds). As a result, updated location information 128 may be generated, movement parameters 130 may be recalculated based on that updated location information 128, and a subsequent determination regarding whether the particular dairy cow 104 is likely to be in estrus may be made (in a manner substantially similar to that described above). As yet another example, controller 116 may access location information for other dairy cows 104 in free stall pen 102 to identify those other dairy cows 104 within a predefined distance of the particular dairy cow 104 in order to determine (1) whether any dairy cow 104 located near the particular dairy cow 104 is mounting the particular dairy cow 104 and/or (2) whether the particular dairy cow 104 is a member of a SAG (each of which is described above with regard to FIG. 1). At step 216, the method ends.

Although the steps of method 200 have been described as being performed in a particular order, the present disclosure contemplates that the steps of method 200 may be performed in any suitable order, according to particular needs.

Figure 3:
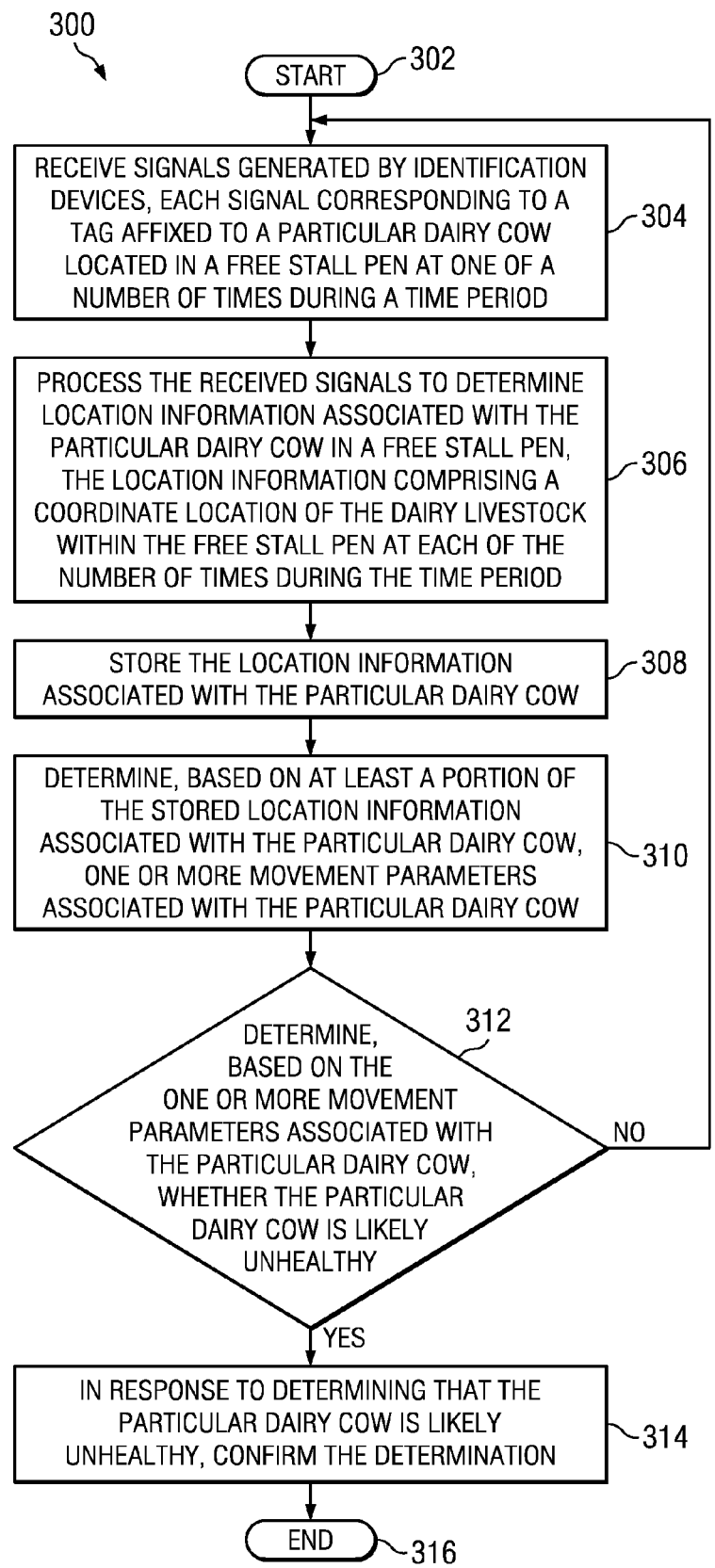
FIG. 3 illustrates an example method for health monitoring using real-time location, according to certain embodiments of the present disclosure.

FIG. 3 illustrates an example method 300 for health monitoring, according to certain embodiments of the present disclosure. Although method 300 is described with regard to a particular dairy cow 104, the present disclosure contemplates a substantially similar method being performed with regard to each of the plurality of dairy cows 104 in free stall pen 102.

The method begins at step 302. At step 304, controller 116 receives signals generated by a number of the identification devices 114 positioned at various locations in and/or around free stall pen 102. At step 306, controller 116 processes the received signals (e.g., using RTL logic 122, described above) to determine location information 128 associated with the particular dairy cow 104. At step 308, controller 116 may store the determined location information 128 associated with the particular dairy cow 104 (e.g., in memory module 120). Steps 304-308 may be performed in a substantially similar manner to steps 204-208, described above with regard to FIG. 2.

At step 310, controller 116 may determine one or more movement parameters 130 associated with the particular dairy cow 104 (e.g., using health monitoring logic 126, described above) based on at least a portion of the stored location information 128 associated with the particular dairy cow 104. For example, the determined movement parameters may include a stall standing parameter 134, a stall lying parameter 136, an alley walking parameter 138, an alley lying parameter 140, an alley standing parameter 142, a watering parameter 144, a feeding parameter 146, a watering count 148, and/or feeding count 150 (each of which are described above with respect to FIG. 1).

At step 312, controller 116 may determine whether the particular dairy cow 104 is likely unhealthy (e.g., using health monitoring logic 126, described above) based on the one or more movement parameters 130 associated with the particular dairy cow 104. For example, controller 116 may determine whether the particular dairy cow 104 is likely unhealthy by comparing a health index for the particular dairy cow 104 with a baseline health index. If the health index for particular dairy cow 104 is greater than the baseline health index by more than a predefined amount (e.g., 250%), controller 116 may determine that the particular dairy cow 116 is likely unhealthy. In embodiments in which the health index corresponds to a function of a stall standing parameter 134, a stall lying parameter 136, an alley walking parameter 138, an alley lying parameter 140, an alley standing parameter 142 a watering parameter 144, a feeding parameter 146, a watering count 148, and/or a feeding count 150, an increase in activity in certain portions of free stall pen 102 (e.g., an increase in the amount of time spent lying in walking alleys 108) may be an indicator that the particular dairy cow 104 is unhealthy.

If controller 116 determines at step 312 that the particular dairy cow 104 is likely unhealthy, the method proceeds to step 314. Otherwise, the method ends at step 316. At step 314, controller 116 may confirm the determination that the particular dairy cow 104 is likely unhealthy. For example, controller 116 may initiate the generation of a signal to be communicated to identification devices 114, the signal causing identification devices 114 to increase the frequency with which the tag of the particular dairy cow 104 is read (e.g., from fifteen seconds to five seconds). As a result, updated location information 128 may be generated, movement parameters 130 may be recalculated based on that updated location information 128, and a subsequent determination regarding whether the particular dairy cow 104 is likely unhealthy may be made (in a manner substantially similar to that described above). If the subsequent determination also indicates that the particular dairy cow 104 is likely unhealthy, the initial determination may be confirmed. At step 316, the method ends.

Although the steps of method 300 have been described as being performed in a particular order, the present disclosure contemplates that the steps of method 300 may be performed in any suitable order, according to particular needs.

Although the present invention has been described with several embodiments, diverse changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A method for health monitoring, comprising:
    electronically receiving location information associated with a dairy livestock, the location information generated by a plurality of identification devices positioned in a pen that operate in conjunction with a tag worn by the dairy livestock;
    storing the location information associated with the dairy livestock, the location information comprising a location of the dairy livestock within the pen at each of a plurality of times during a first time period;
    determining, based on at least a portion of the stored location information, at least a first movement parameter and a second movement parameter associated with the dairy livestock;
    determining a health index for the dairy livestock corresponding to a function of at least the first movement parameter and the second movement parameter;
    storing a baseline health index over a second time period that is prior to the first time period; and
    determining that the dairy livestock is unhealthy by determining that the determined health index is in excess of the baseline health index by more than a predefined amount.

2. The method of claim 1, wherein communication between the plurality of identification devices and the tag affixed to the dairy livestock is facilitated by ultra-wide band (UWB) technology.

3. The method of claim 1, wherein the location information is generated by triangulating the signals generated by the plurality of identification devices.

4. The method of claim 1, wherein:
    determining one or more movement parameters comprises:
        determining a stall standing parameter corresponding to the percentage of the time period that the dairy livestock was standing in a stall of the free stall pen;
        determining a stall lying parameter corresponding to the percentage of the time period that the dairy livestock was lying in a stall of the free stall pen;
        determining an alley walking parameter corresponding to the percentage of the time period that the dairy livestock was walking in a walking alley of the free stall pen;
        determining an alley lying parameter corresponding to the percentage of the time period that the dairy livestock was lying in a walking alley of the free stall pen;
        determining an alley standing parameter corresponding to the percentage of the time period that the dairy livestock was standing stationary in a walking alley of the free stall pen;

determining a feeding parameter corresponding to the percentage of the time period that the dairy livestock was located within a predefined distance of a feed lane of the free stall pen;

determining a watering parameter corresponding to the percentage of the time period that the dairy livestock was located within a predefined distance of a water trough of the free stall pen; and determining the health index comprises determining a function of the stall standing parameter, the stall lying parameter, the alley walking parameter, the alley lying parameter, the alley standing parameter, the feeding parameter, and the watering parameter.

5. The method of claim 1, wherein the baseline health index comprises an average health index for a plurality of other dairy livestock in the pen.

6. The method of claim 1, wherein the baseline health index comprises a health index for the dairy livestock.

7. A system for health monitoring, comprising:
a plurality of identification devices positioned in a pen;
a tag worn by a dairy livestock in the pen;
one or more memory modules that store:
location information obtained from the identification devices in conjunction with the tag, the location information associated with the dairy livestock, the location information comprising a location of the dairy livestock within the pen at each of a plurality of times during a first time period; and
a baseline health index over a second time period that is prior to the first time period; and
one or more processing modules that:
determines, based on at least a portion of the stored location information, at least a first movement parameter and a second movement parameter associated with the dairy livestock;
determines a health index for the dairy livestock corresponding to a function of at least the first movement parameter and the second movement parameter; and
determines that the dairy livestock is unhealthy by determining that the determined health index is in excess of the baseline health index by more than a predefined amount.

8. The system of claim 7, wherein communication between the plurality of identification devices and the tag affixed to the dairy livestock is facilitated by ultra-wide band (UWB) technology.

9. The system of claim 7, wherein the location information is generated by triangulating the signals generated by the plurality of identification devices.

10. The system of claim 7, wherein:
determining one or more movement parameters comprises:
determining a stall standing parameter corresponding to the percentage of the time period that the dairy livestock was standing in a stall of the free stall pen;
determining a stall lying parameter corresponding to the percentage of the time period that the dairy livestock was lying in a stall of the free stall pen;
determining an alley walking parameter corresponding to the percentage of the time period that the dairy livestock was walking in a walking alley of the free stall pen;
determining an alley lying parameter corresponding to the percentage of the time period that the dairy livestock was lying in a walking alley of the free stall pen;

determining an alley standing parameter corresponding to the percentage of the time period that the dairy livestock was standing stationary in a walking alley of the free stall pen;

determining a feeding parameter corresponding to the percentage of the time period that the dairy livestock was located within a predefined distance of a feed lane of the free stall pen;

determining a watering parameter corresponding to the percentage of the time period that the dairy livestock was located within a predefined distance of a water trough of the free stall pen; and determining the health index comprises determining a function of the stall standing parameter, the stall lying parameter, the alley walking parameter, the alley lying parameter, the alley standing parameter, the feeding parameter, and the watering parameter.

11. The system of claim 7, wherein the baseline health index comprises an average health index for a plurality of other dairy livestock in the pen.

12. The system of claim 7, wherein the baseline health index comprises a health index for the dairy livestock.

13. A method for health monitoring, comprising:
storing location information associated with a dairy livestock, the location information comprising a coordinate location of the dairy livestock within a free stall pen at each of a plurality of times during a time period, the location information having been generated by a real-time location system (RTLS) comprising a plurality of identification devices positioned throughout the free stall pen, the plurality of identification devices each operable to, at each of the plurality of times during the time period, generate a signal corresponding to a tag affixed to the dairy livestock;

determining a stall standing parameter corresponding to the percentage of the time period that the dairy livestock was standing in a stall of the free stall pen;

determining a stall lying parameter corresponding to the percentage of the time period that the dairy livestock was lying in a stall of the free stall pen;

determining an alley walking parameter corresponding to the percentage of the time period that the dairy livestock was walking in a walking alley of the free stall pen;

determining an alley lying parameter corresponding to the percentage of the time period that the dairy livestock was lying in a walking alley of the free stall pen;

determining an alley standing parameter corresponding to the percentage of the time period that the dairy livestock was standing stationary in a walking alley of the free stall pen;

determining a feeding parameter corresponding to the percentage of the time period that the dairy livestock was located within a predefined distance of a feed lane of the free stall pen;

determining a watering parameter corresponding to the percentage of the time period that the dairy livestock was located within a predefined distance of a water trough of the free stall pen; and determining whether a heath index for the dairy livestock is in excess of a baseline health index by more than a predefined amount, the health index for the dairy livestock corresponding to a function of the stall standing parameter, the stall lying parameter, the alley walking parameter, the alley lying parameter, the alley standing parameter, the feeding parameter, and the watering parameter.

* * * * *